United States Patent [19]
Takamatsu et al.

[11] Patent Number: 5,619,326
[45] Date of Patent: Apr. 8, 1997

[54] METHOD OF SAMPLE VALUATION BASED ON THE MEASUREMENT OF PHOTOTHERMAL DISPLACEMENT

[75] Inventors: Hiroyuki Takamatsu; Tsutomu Morimoto; Shingo Sumie; Naoyuki Yoshida, all of Kobe, Japan

[73] Assignee: Kabushiki Kaisha Kobe Seiko Sho, Kobe, Japan

[21] Appl. No.: 409,670

[22] Filed: Mar. 24, 1995

[30] Foreign Application Priority Data

Mar. 25, 1994 [JP] Japan .................. 6-055357
Jan. 13, 1995 [JP] Japan .................. 7-003721

[51] Int. Cl.$^6$ .................. G01B 9/02
[52] U.S. Cl. .................. 356/357; 356/349; 356/432
[58] Field of Search .................. 356/351, 357, 356/349, 432; 73/655, 656, 657

[56] References Cited

U.S. PATENT DOCUMENTS 5,083,869 1/1992 Nakata et al. .
5,298,970 3/1994 Takamatsu et al. .
5,377,006 12/1994 Nakata .................. 356/357
5,479,259 12/1995 Nakata et al. .................. 356/349

FOREIGN PATENT DOCUMENTS 7-27746 1/1995 Japan .

OTHER PUBLICATIONS

Huang et al, "Dual–Probe Interferometer", Sep. 1991, Journal of Acoustical Society of America, pp. 1269–1274.
Applied Optics, vol. 22, No. 18, Sep. 15, 1983, pp. 2882–2886, L. C. M. Miranda, "Photodisplacement Spectroscopy of Solids: Theory".

*Primary Examiner*—Georgia Y. Epps
*Assistant Examiner*—Robert Kim
*Attorney, Agent, or Firm*—Oblon, Spivak, McClelland, Maier & Neustadt, P.C.

[57] ABSTRACT

A sample evaluation method based on the measurement of photothermal displacement in which two exciting light beams and two measuring light beams are produced by a laser source, the exciting beams are rendered intensity modulation in opposite phase relationship by an acoustic-optic modulator and illuminated to different positions of a sample, the measuring beams are provided with different oscillation frequencies by acoustic-optic modulators and illuminated to the irradiation positions of the exciting beams correspondingly, the reflected lights of measuring beams from the sample are merged so as to interfere with each other, and the sample is evaluated based on the phase of the interference light. The method is capable of measuring the photothermal displacement accurately and stably without implementing intricate signal processings.

9 Claims, 6 Drawing Sheets

(VARIANT OF PORTION A IN FIG.1)

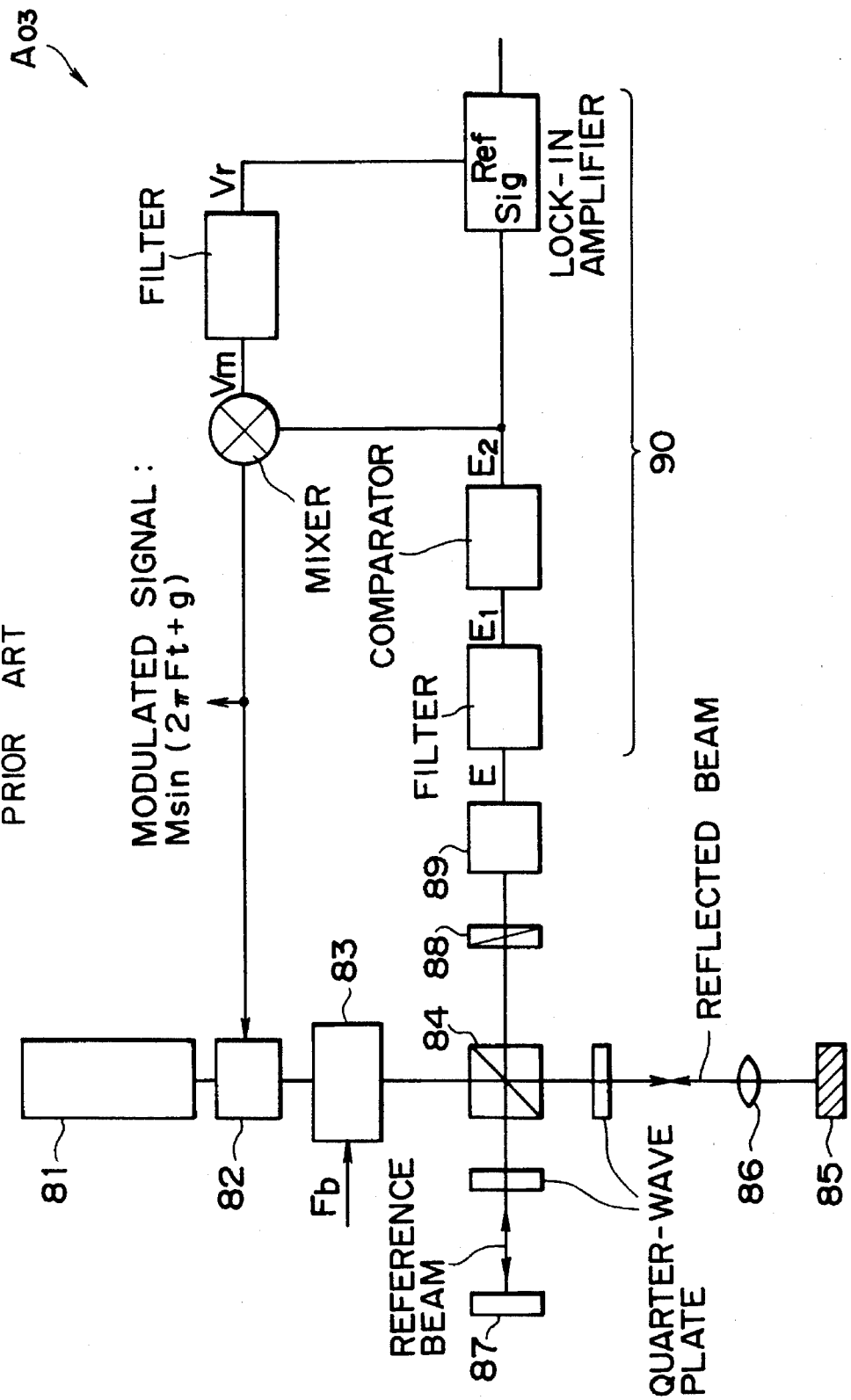

METHOD OF SAMPLE VALUATION BASED ON THE MEASUREMENT OF PHOTOTHERMAL DISPLACEMENT

BACKGROUND OF THE INVENTION

1. Field of the Invention

The present invention relates to a method of sample valuation in which an intensity-modulated excitation light beam is illuminated periodically on to a sample and thermal expansion vibration emerging on the surface of the sample is measured thereby to evaluate the sample for the inspection of defects or the like.

2. Description of the Prior Art

When a light beam which is modulated periodically in terms of the intensity (exciting beam) is illuminated to a sample, it heats up by absorbing the light and develops thermal expansion. Due to the periodical intensity modulation of the illuminated light, the sample undergoes periodic variation of temperature, causing thermal expansion vibration to occur. This thermal response is measured, as it is known to be the technique of measuring the photothermal displacement, thereby valuating the sample.

FIG. 5 shows in brief the arrangement of a prior art apparatus A01 for measuring the thermal expansion vibration of a sample based on the Michelson's laser interference method (described in Miranda, APPLIED OPTICS, Vol. 22, No. 18, p. 2882, (1983)). In the figure, reference numeral 61 denotes a sample under test, 62 is an excitation light source and 63 is a chopper which renders intensity modulation to a light beam emitted by the light source 62, with the modulated beam being illuminated to the sample 61 so that the irradiated sample 61 develops thermal expansion vibration.

For the measurement of this thermal expansion vibration (photothermal displacement) based on the scheme of laser interference, a light beam from a measuring laser source 64 is split by a half mirror 65 into a light beam directed to the thermal expansion measuring position of the sample and a light beam directed to a fixed mirror 66. The reflected lights from the sample 61 and the mirror 66 interfere with each other, and the resulting interference light is received by an opto-electric transducer 67, which produces an electrical output E expressed as follows.

$$E = C_1 + C_2 \cdot cos(P(t) + \phi) \tag{1'}$$

where $C_1$, $C_2$ and $\phi$ are constants dependent on the structure of the interferometer, opto-electric conversion factor, etc., and P(t) is the phase variation attributable to the displacement of the sample surface due to the thermal expansion vibration caused by the illumination of the exciting beam. A signal processing circuit 68 is used to measure the thermal expansion vibration, and the characteristic of thermal elasticity of the sample is evaluated.

FIG. 6 shows in brief the arrangement of part of a prior art apparatus A02 which is based on the scheme of using the exciting beam also for the measuring beam (Japanese Patent Application No.5-172948) and was developed by the inventors of the present invention.

In the figure, an exciting beam from an excitation light source 72 is rendered intensity modulation by an acoustic-optic modulator 73, and a resulting diffracted and non-diffracted light beams are illuminated to different positions of a sample 71 by way of a beam splitter 74. The reflected lights from the irradiation positions go back through the beam splitter 74 and interfere with each other in an interferometer made up of mirrors M and a beam splitter 77. The resulting interference light is received by an opto-electric transducer 78, which produces an electrical output E expressed as follows.

$$E = C_3 + C_4 \cdot A(t) \cdot cos\{2\pi F b t + P(t) + \phi\} \tag{2'}$$

where $C_3$, $C_4$ and $\phi$ are constants dependent on the structure of the interferometer, opto-electric conversion factor, etc., and A(t) is a factor dependent on the degree of intensity variation produced by the acoustic-optic modulator 73, Fb is the carrier wave frequency of the acoustic-optic modulator 73, and P(t) is the phase variation attributable to the photothermal displacement of the sample caused by the illumination of exciting beam. A signal processing circuit 79 is used to measure the thermal expansion vibration, and the characteristic of thermal elasticity of the sample is evaluated.

In this prior art apparatus A02, the diffracted and non-diffracted light beams are rendered intensity modulation in opposite phase relationship, causing the photothermal displacement pertinent to the reflected lights from the sample 71 to produce a phase difference twice that of the prior art apparatus A01, and the accuracy of measuring the photothermal displacement is enhanced.

FIG. 7 shows in brief the arrangement of a prior art apparatus A03 which is based on the scheme of using the exciting beam also for the measurement (Japanese patent publication JP-A-3-269346) and was developed by the inventors of the present invention prior to the above-mentioned apparatus A02.

In the figure, an exciting beam from an excitation light source 81 is rendered intensity modulation by an acoustic-optic modulator 82. The modulated beam is fed to a frequency shifter 83, by which beams 1 and 2 that are orthogonal to each other and have a frequency difference of Fb are produced. These beams are separated by a beam splitter 84. The beam 1 is illuminated on to a sample 85 through a lens 86, and the beam 2 is directed to a mirror 87 to become a reference light beam.

The reflected light from the sample 85 and the reference beam interfere with each other by being fed through the beam splitter 84 and a polarizing plate 88, and the resulting interference light is received by an opto-electric transducer 89. The transducer 89 produces an output E, which includes the term of phase variation P(t) attributable to the photothermal displacement of the sample caused by the illumination of exciting beam, as expressed by the above equation 2'. A signal processing circuit 90 is used to measure the thermal expansion vibration, and the characteristic of thermal elasticity of the sample is evaluated.

However, the foregoing prior art sample valuation methods based on the measurement of photothermal displacement have the following problems.

(1) The prior art apparatus A01 necessitates to direct the measuring beam to the irradiation position of the exciting beam on the sample. The misalignment of these light beams creates the fluctuation of measured value of the photothermal displacement, and it cannot be measured stably and accurately. When the photothermal displacement is small, the phase variation detected based on the interference measurement is also small, resulting in a degraded accuracy of measurement.

(2) The prior art apparatus A02 and A03 use the exciting beam also for the measuring beam, and accordingly the misalignment of two light beams in the case of the apparatus A01 is dissolved. The apparatus A02 can have the enhanced measuring accuracy as mentioned previously even if the photothermal displacement is small. However, any of these apparatus A02 and A03 creates a phase variation in the electrical signal due to a phase variation in the intensity-modulated beam of the acoustic-optic modulator and a signal level variation of the opto-electric transducer or amplifier. This phase variation will become a noise component superimposed on the phase variation attributable to the photothermal displacement. On this account, both apparatus need to implement intricate signal processings for the noise compensation in order to perform the stable measurement of photothermal displacement.

SUMMARY OF THE INVENTION

The present invention is intended to solve the foregoing prior art problems, and its prime object is to provide an improved method of sample valuation based on the measurement of photothermal displacement, the method being capable of performing the accurate and stable measurement without the need of intricate signal processings.

In order to achieve the above objective, the first of the present invention resides in the method of valuating a sample by illuminating an excitation light beam on to the sample and measuring by use of a measuring light beam the photothermal displacement of the sample caused by the excitation light beam, wherein two exciting beams are generated, rendered intensity modulation in different phase relationship and illuminated to different positions of the sample, two measuring beams are generated, provided with different oscillation frequencies and illuminated to the irradiation positions of the two exciting beams, the reflected measuring beams from the sample are merged so as to interfere with each other, and the sample is evaluated based on the phase of the interference light.

The invention also resides in the method of sample valuation based on the measurement of photothermal displacement, wherein the two exciting beams are rendered intensity modulation in opposite phase relationship.

The invention also resides in the method of sample valuation based on the measurement of photothermal displacement, wherein the exciting beams are provided with an oscillation frequency different from those of the measuring beams.

The invention also resides in the method of sample valuation based on the measurement of photothermal displacement, wherein a diffracted and non-diffracted light beams resulting from intensity modulation for the two exciting beams by an acoustic-optic modulator are used as exciting beams.

The invention also resides in the method of sample valuation based on the measurement of photothermal displacement, wherein the photothermal displacement of the sample is measured based on the phase variation of a beat signal included in the opto-electric conversion output for the interference light and having a component of oscillation frequency difference of the two measuring beams.

The invention also resides in the method of sample valuation based on the measurement of photothermal displacement, wherein the exciting beams are generated by means of a variable-wavelength light source.

The second of the present invention resides in the method of valuating a sample by illuminating an excitation light beam on to the sample and measuring the photothermal displacement of the sample caused by it, wherein an intensity-modulated light beam is split into two beams, one beam is illuminated on to the sample, the phase of the reflected light from the sample is measured by making reference to another split beam, and the photothermal displacement is measured based on the measured phase of the reflected light.

The invention also resides in the method of sample valuation based on the measurement of photothermal displacement, wherein another light beam having a different light frequency from that of the split beams is generated, it is merged with the reflected light and the other split beam so as to interfere with each other separately, and the photothermal displacement is measured based on the phase difference of the interference lights.

The invention also resides in the method of sample valuation based on the measurement of photothermal displacement, wherein the interference lights are received by separate opto-electric transducers, and the photothermal displacement is measured based on the phase difference of the output signals of the transducers.

According to the first invention for valuating a sample by illuminating an excitation light beam on to the sample and measuring by use of a measuring light beam the photothermal displacement of the sample caused by the excitation light beam, two exciting beams and two measuring beams are generated initially. The exciting beams are rendered intensity modulation in different phase relationship and illuminated to different positions of the sample. The measuring beams are provided with different oscillation frequencies and illuminated to the positions of illumination of the exciting beams. The reflected measuring beams from the sample are merged so as to interfere with each other, and the sample is evaluated based on the phase of the interference light.

Accordingly, based on the illumination of the exciting beams that are intensity-modulated in different phase relationship to the sample, the phase difference of measuring beams attributable to the photothermal displacement at the excitation positions is greater than the case of single beam excitation of the prior art apparatus A01, and consequently the sensitivity of detection of the photothermal displacement rises. The measuring beams are not rendered intensity modulation by an acoustic-optic modulator which is the case of the prior art apparatus A02, and the creation of phase noise by the modulator is prevented and consequently the photothermal displacement can be measured stably.

Alternatively, the two exciting beams are rendered intensity modulation in opposite phase relationship. In this case, the reflected measuring beams from the sample have a phase difference twice as large as the case of single beam excitation, and the sensitivity of the detection of photothermal displacement is raised and consequently the measuring accuracy is enhanced.

Alternatively, the exciting beams are provided with an oscillation frequency different from those of the measuring beams. In this case, a phase variation component resulting from the photothermal displacement of the sample is extracted from the reflected light more reliably and consequently the measuring accuracy is enhanced.

Alternatively, the two exciting beams are reformed into a diffracted and non-diffracted light beams through intensity modulation by means of an acoustic-optic modulator so that the resulting exciting beams have opposite phase relationship. This is the case of the highest sensitivity of the detection of photothermal displacement, and consequently the measuring accuracy is enhanced.

Alternatively, the photothermal displacement of the sample is measured based on the phase variation of a beat signal included in the opto-electric conversion output of the interference light and having a component of oscillation frequency difference of the two measuring beams. Consequently, a phase variation component is extracted more reliably and the measuring accuracy is enhanced.

Alternatively, the exciting beams are generated by means of a variable-wavelength light source, and in this case spectrometric valuation of a sample is made possible.

According to the second invention for valuating a sample by illuminating a light beam on to the sample and measuring the photothermal displacement of the sample caused by it, an intensity-modulated light beam is split into two beams initially. One beam is illuminated on to the sample. The phase of the reflected light from the sample is measured by making reference to another split beam, and the photothermal displacement is measured based on the measured phase of the reflected light.

Accordingly, the phase variation created by the intensity modulation of light beams cancels out, eliminating the phase noise of the acoustic-optic modulator encountered in the prior art apparatus A02 and A03. Consequently, the photothermal displacement can be measured stably.

Alternatively, another light beam having a different light frequency from that of the split beams is generated and merged with the reflected light and the other split beam so as to interfere with each other separately, and the photothermal displacement is measured based on the phase difference of the interference light. In this case, the reflected light and the other light beam have their light frequencies undergoing beat-down (reduction) by use of the light having a different light frequency from that of these light beams, and consequently the accuracy of phase difference measurement is ensured.

Alternatively, the interference lights are received by separate opto-electric transducers, with the photothermal displacement being measured based on the phase difference of the output signals of the transducers. In this case, the beat-down light beams are converted into a.c. signals so that their phase difference is measured, and consequently the accuracy of phase difference measurement is ensured. Consequently, the photothermal displacement can be measured accurately and stably without the need of intricate signal processings.

BRIEF DESCRIPTION OF THE DRAWINGS

FIG. 7 is a block diagram showing the principal arrangement of the third prior art sample valuation apparatus (A03) based on the measurement of photothermal displacement.

DESCRIPTION OF THE PREFERRED EMBODIMENTS

Specific embodiments of the present invention will be explained with reference to the drawings.

The sample valuation method based on the measurement of photothermal displacement according to the first invention is identical to the prior art (apparatus A01 and A02) in that an excitation light beam is illuminated on to a sample and the photothermal displacement of the sample caused by the exciting beam is measured by use of a measuring light beam thereby to evaluate the sample. However, the first invention is different from the prior art in that two exciting beams are generated, rendered intensity modulation in different phase relationship and illuminated to different positions of the sample, two measuring beams are generated, provided with different oscillation frequencies and illuminated to the irradiation positions of the two exciting beams, the reflected measuring lights from the sample are merged so as to interfere with each other, and the sample is evaluated based on the phase of the interference light.

The basic principle of the first inventive method will be explained in connection with the apparatus A1 of the first embodiment.

Figure 1:
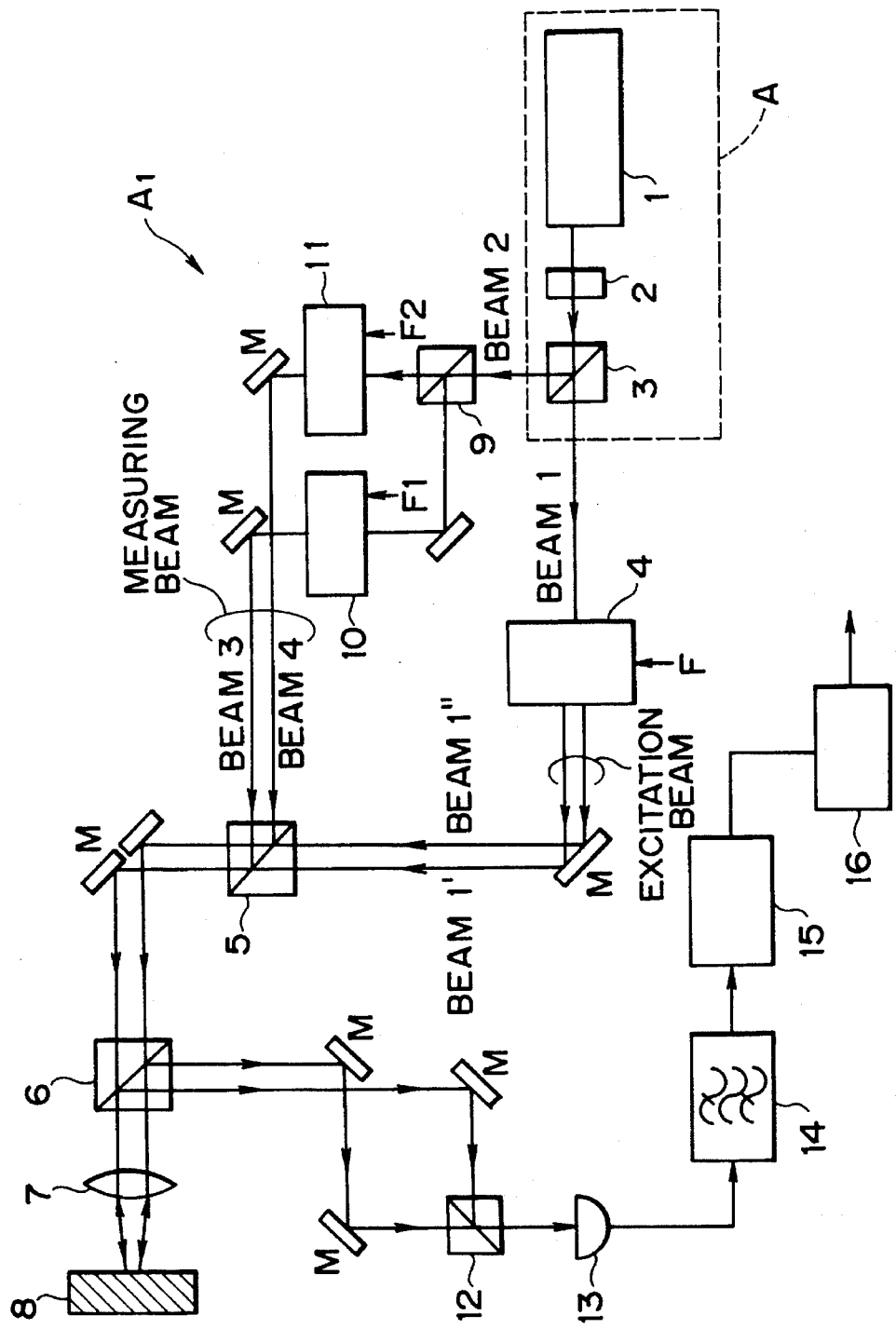
FIG. 1 is a block diagram showing the principal arrangement of the sample valuation apparatus (A1) based on the measurement of photothermal displacement according to an embodiment of the first of the present invention (first embodiment)

In the apparatus A1 shown in FIG. 1, a linearly polarized laser beam from a laser source (YAG laser) 1 is split in certain proportion into beams 1 and 2 by means of a halfwave plate 2 and polarizing beam splitter 3. The beam 1 is used for the exciting beam, and is rendered periodic intensity modulation at frequency F by an acoustic-optic modulator 4. The acoustic-optic modulator 4 produces output beams, i.e., a diffracted laser beam (1st-order diffracted light) and non-diffracted laser beam (0th-order diffracted light), which are conducted by mirrors M, polarizing beam splitter 5 and beam splitter 6, and illuminated by a lens 7 on to a sample 8. The positions of the sample 8 where the 0th-order and 1st-order diffracted laser beams are illuminated are dependent on their incident beam angle at the lens 7 and the focal distance of the lens 7. In this embodiment, the 0th-order and 1st-order diffracted laser beams are illuminated at a spacing of about 100 μm on the sample 8. The 0th-order and 1st-order diffracted laser beams are intensity-modulated in opposite phase relationship, and therefore the photothermal displacements caused by these excitation light beams also have opposite phase relationship.

The photothermal displacements are measured with the beam 2 that has been split by the polarizing beam splitter 3. The beam 2 is further split by a beam splitter 9 into two beams, and the split beams are rendered frequency shifting by acoustic-optic modulators 10 and 11 which are driven steadily by carrier waves of frequencies F1 and F2. The diffracted laser beams produced by the acoustic-optic modulators 10 and 11 have their frequencies shifted by the amount of F1 and F2, respectively, from their original frequency. The resulting beams 3 and 4, which are used as measuring beams, are directed to the polarizing beam splitter 5 so as to be coaxial with the 0th-order and 1st-order diffracted laser beams 1' and 1", respectively, and then illuminated to the sample 8 (measuring positions of photothermal displacements).

The reflected lights of the beams 3 and 4 from the sample 8 are conducted back through the lens 7 and beam splitter 6, and merged by mirrors M and a beam splitter 12 so as to interfere with each other. The resulting interference light is received by an opto-electric transducer 13. From the output signal of the transducer 13, an interference signal component V (component of frequency F1–F2) of the beams 3 and 4 is extracted with a filter 14. The extracted signal is shaped to have a constant amplitude by a limitter amplifier 15, which produces an output V expressed as follows.

$$V = C \cdot \sin\{2\pi(F1-F2)t + 4\pi L0/\lambda - 4\pi L1/\lambda + P\} \quad (1)$$

where C and P are constants, k is the wavelength of beams 3 and 4, and L0 and L1 are photothermal displacements caused by the beams 1' and 1". If the beams 1' and 1" have an equal intensity and the intensity variation is in opposite phase relationship as mentioned previously, the output V is expressed as follows.

$$V = C \cdot \sin\{2\pi(F1-F2)t + 2 \times 4\pi L0/\lambda + P\} \quad (2)$$

The photothermal displacement is evaluated through the detection of the phase of output V by means of an FM demodulation circuit 16. As it is revealed by the above equation 2 that the phase variation of the interference signal caused by the photothermal displacement is twice as large as that of single excitation (result of illumination of only the 0th-order diffracted laser beam or 1st-order diffracted laser beam), the sensitivity of measurement is high even in the case of a small photothermal displacement.

Practically, the two exciting beams 1' and 1" do not need to be in exactly opposite phase relationship in which case the sensitivity is highest, but it is sufficient for the beams to be at least out of phase with each other.

It is necessary to set the carrier frequencies of the acoustic-optic modulators 4, 10 and 11 so that the excitation noise is not mixed to the output V. In this embodiment, one exciting beam 1' (0th-order diffracted light) has its light frequency set to FP MHz, another exciting beam 1" (1st-order diffracted light) is set to FP-120 MHz, one measuring beam 3 is set to FP+120 MHz, and another measuring beam 4 is set to FP+200 MHz. The resulting interference signal of the beams 3 and 4 will have beat frequencies of 120, 200, 240 and 320 MHz, and these frequency components can readily be removed electrically by the filter 14, and only the interference signal component of 80 MHz can surely extracted. Frequency settings other than those mentioned above are of course possible, with at least the oscillation frequency being set differently between the exciting beams 1' and 1" and the measuring beams 3 and 4 so that the interference signal component is extracted easily.

The spacing of the irradiation positions of the two exciting beams 1' and 1" on the sample 8, which is about 100 μm in this embodiment, can be set arbitrarily, provided that it must be greater than the length of thermal diffussion on the sample 8 so that completely differential photothermal displacements emerge. The smaller the spacing of irradiation positions, the higher resolution of sample valuation can be expected. The use of laser beams for the exciting beams and measuring beams in this embodiment allows a minimal spacing of the illumination positions.

Figure 2:
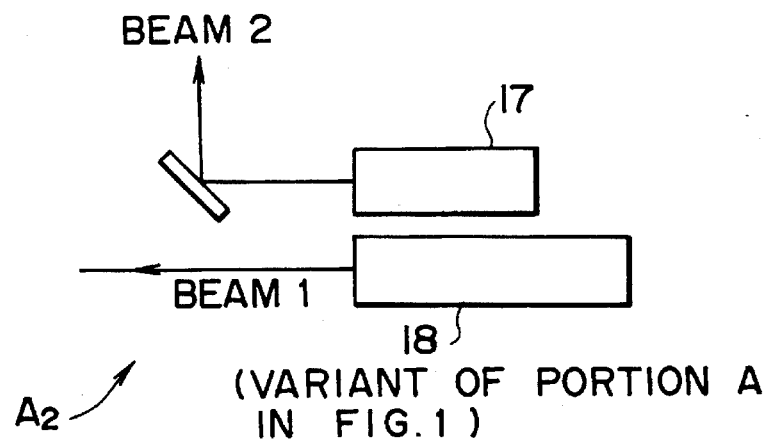
FIG. 2 is a block diagram showing part of the sample valuation apparatus (A2) according to another embodiment of the first invention (second embodiment)

FIG. 2 shows the sample valuation apparatus A2 based on the measurement of photothermal displacement according to the second embodiment of this invention, in which separate laser sources are used to generate an exciting beam and measuring beam, in contrast to the first embodiment of using a common laser source. An excitation light source 18 is a tunable laser source (e.g., dye laser, etc.), and a measuring light source 17 is a YAG laser similar to that used in the preceding first embodiment. The remaining arrangement is identical to the apparatus A1 of the first embodiment. The apparatus A2 is accordingly operative to produce photothermal displacements by using excitation light beams of different wavelengths and capable of performing the spectrometric valuation of a sample 8 based on the measurement of photothermal displacements.

Figure 3:
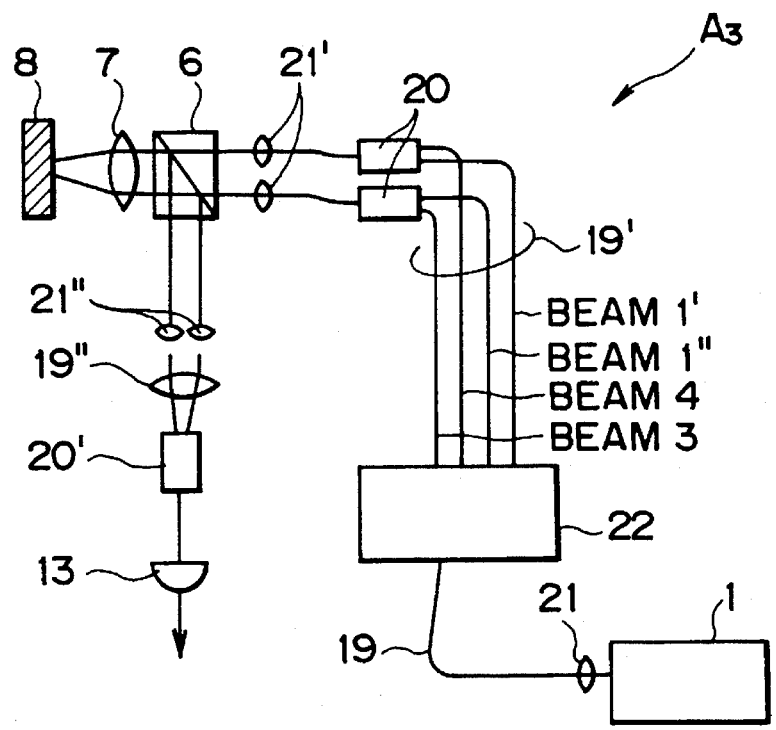
FIG. 3 is a block diagram showing part of the sample valuation apparatus (A3) according to still another embodiment of the first invention (third embodiment)

FIG. 3 shows the sample valuation apparatus AS based on the measurement of photothermal displacement according to the third embodiment of this invention, in which optical fibers are used to lead the laser beams, in contrast to the preceding first and second embodiments in which the laser beams are propagated in the space.

In the figure, a laser beam emitted by a YAG laser 1 is put into an optical fiber 19 by means of a collimator lens 21, and the laser beam is led to a multi-channel acoustic-optic modulator 22. The acoustic-optic modulator 22 produces exciting beams 1' and 1" and measuring beams 3 and 4 from the input laser beam. The laser beams are led by optical fibers 19' to a pair of fiber couplers 20, one merging the beams 1' and 4 and the other merging the beams 1" and 3.

The merged laser beams are released into the space through a pair of collimator lenses 21', conducted by a beam splitter 6, and illuminated by a lens 7 on to the sample 8. The reflected beams from the sample 8 are conducted through the lens 7 and beam splitter 6 and put into optical fibers 19" by a pair of collimator lenses 21". The beams are merged by a fiber coupler 20' so as to interfere with each other, and the interference light is received by an opto-electric transducer 13. The remaining arrangement and operation are completely identical to the apparatus A1 of the first embodiment. In the apparatus A3 of this embodiment, most of the light paths are protected by the optical fibers against external disturbing lights, and consequently the measuring accuracy is enhanced.

Although in the preceding first through third embodiments, the photothermal displacements of the sample are measured based on the phase variation of a beat signal included in the opto-electric conversion output of the interference light and having a component of oscillation frequency difference of the two measuring beams, the practical measurement may be based on the detection of the side band. In this case, a spectrum analyzer is used for the accurate measurement.

According to the first through third embodiments, in which the exciting beams modulated in different phase relationship are ted on to the sample, the reflected measuring beams from the positions of photothermal displacement have a greater phase difference than the case of single-beam excitation of the prior art apparatus A01 and consequently the sensitivity of the detection of photothermal displacement rises. The laser beams used for the measurement of photothermal displacements are not rendered intensity modulation by an acoustic-optic modulator, which is the case of the prior art apparatus A02, and therefore the phase noise caused by the modulator is eliminated and the photothermal displacements can be measured stably. In consequence, it is possible to measure the photothermal displacement accurately and stably without implementing intricate signal processings.

The foregoing first through third embodiments are somewhat complicated in their optical systems because a light beam is split, with one beam being intensity-modulated to become excitation beams and another beam being frequency-shifted to become measuring beams, and thereafter these beams are merged and illuminated on to a sample. The second invention, which will be explained in the following, is intended to simplify the optical system.

The sample valuation method based on the measurement of photothermal displacement according to the second invention is identical to the prior art methods (apparatus A01, A02 and A03) in that a light beam is illuminated to a sample and the photothermal displacement of the sample caused by it is measured thereby to evaluate the sample. However, the fourth embodiment is different from the prior art methods in that an intensity-modulated light beam is split, with one beam being illuminated on to the sample, and the phase of the reflected light is measured by making reference to the phase of the other split beam thereby to measure the photothermal displacement based on the phase of the reflected beam.

Alternatively, another light beam having a different light frequency from that of the split beams is generated and merged with the reflected light beam and the other split beam separately so that each pair of beams interfere, and the photothermal displacement is measured based on the phase difference of these interference lights. This variant method is also different by itself from the prior art methods. Instead of using the light beams of different light frequencies, the phase of the reflect light and the phase of the other split beam may be measured directly at a high frequency region.

The basic principle of the second invention will be explained in connection with the apparatus A4 of the fourth embodiment.

Figure 4:
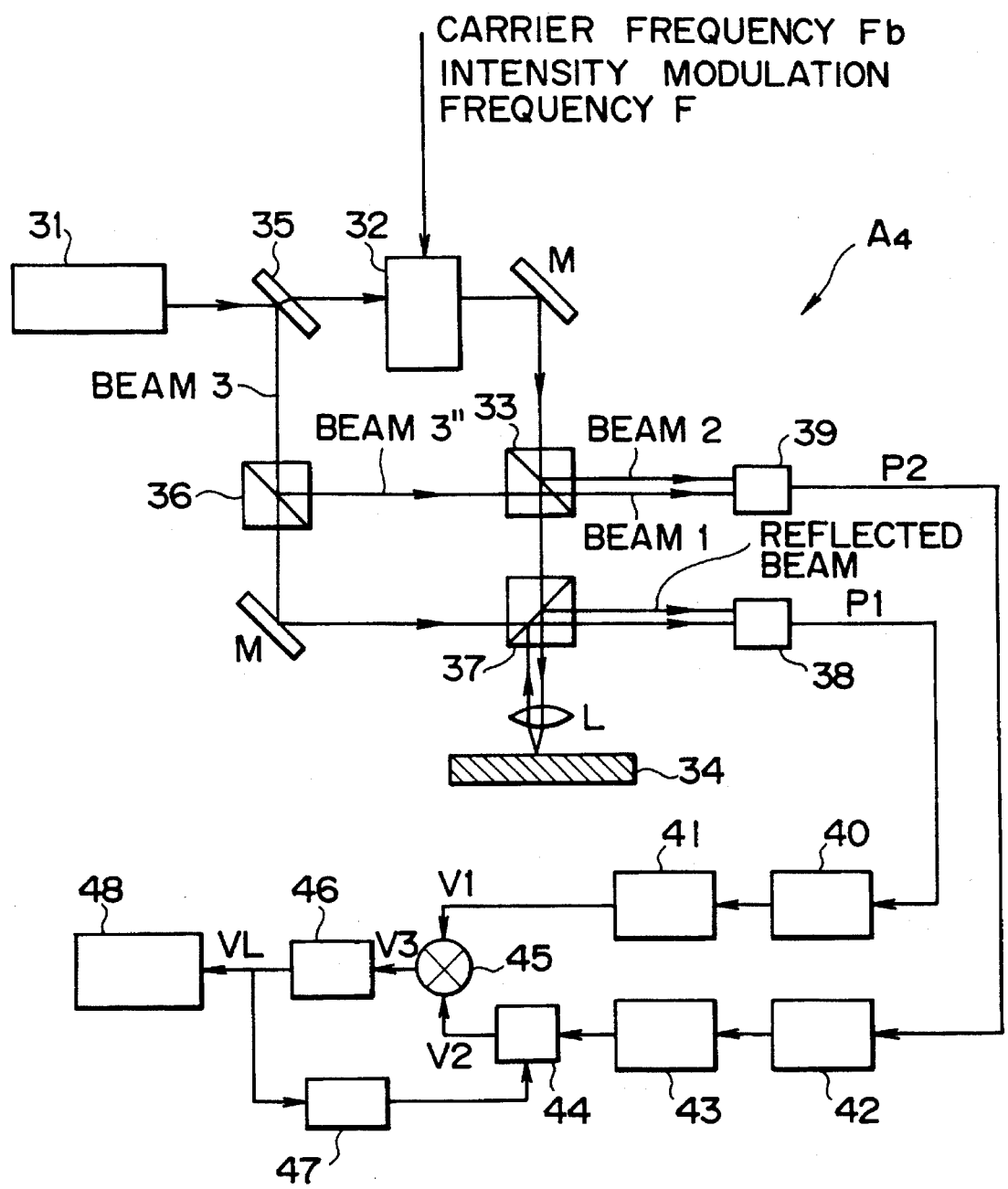
FIG. 4 is a block diagram showing the principal arrangement of the sample valuation apparatus (A4) based on the measurement of photothermal displacement according to one embodiment of the second of the present invention (fourth embodiment)
Figure 5:
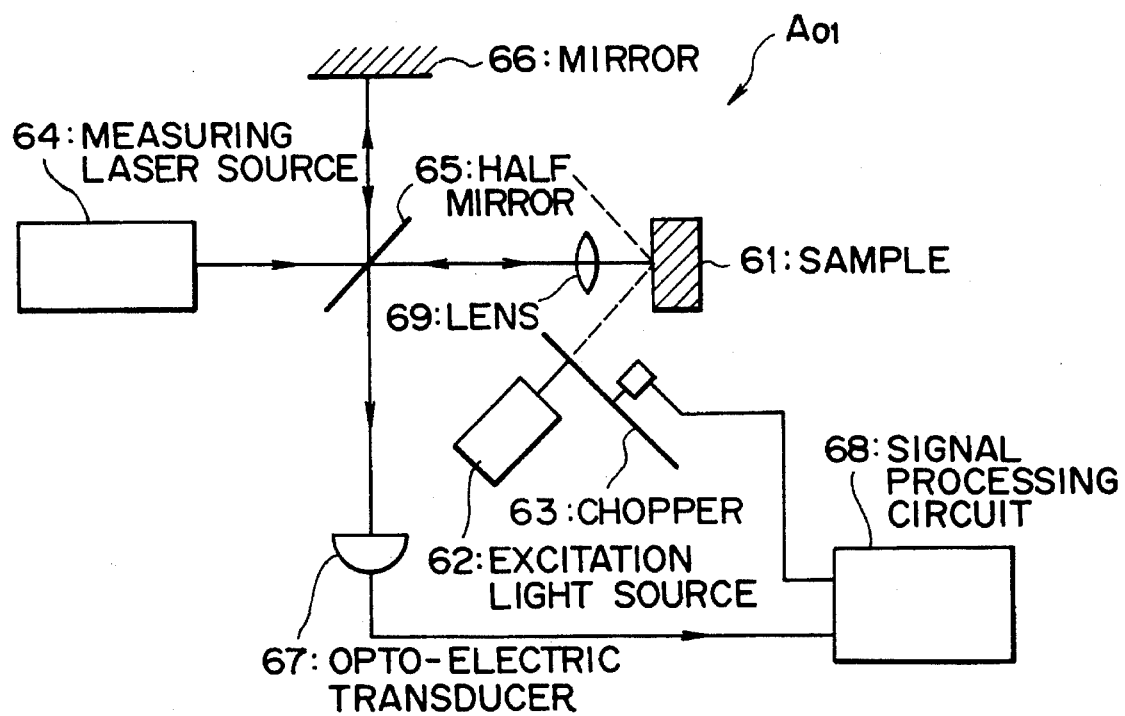
FIG. 5 is a block diagram showing the principal arrangement of the first prior art sample valuation apparatus (A01) based on the measurement of photothermal displacement.
Figure 6:
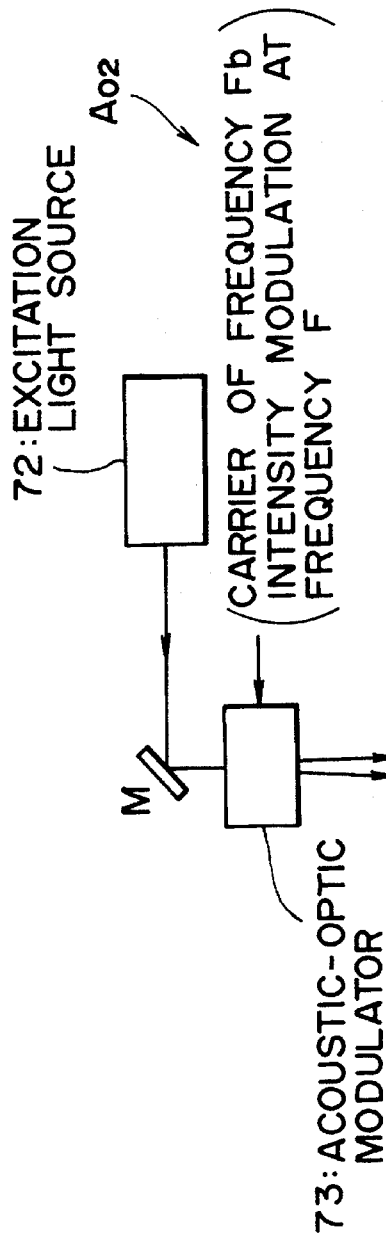
FIG. 6 is a block diagram showing the principal arrangement of the second prior art sample valuation apparatus (A02) based on the measurement of photothermal displacement.
Figure 6:
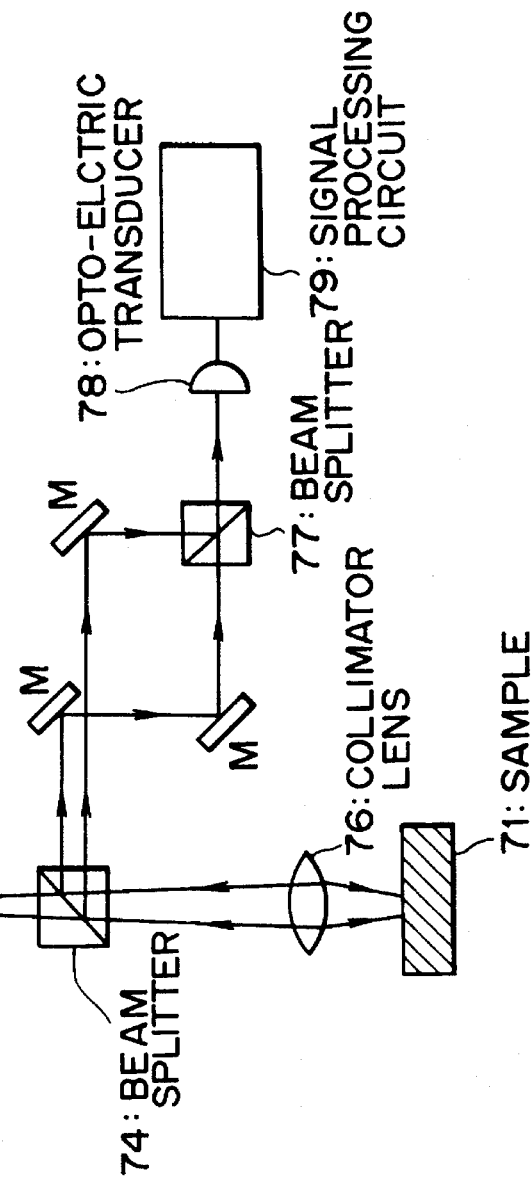

In the apparatus A4 shown in FIG. 4, a laser beam emitted by a YAG laser source 31 with light frequency Fp is rendered intensity modulation by an acoustic-optic modulator 32 which is driven at carrier frequency Fb. The modulated laser beam (diffracted laser beam produced by the modulator 32) is split by a beam splitter 33 into beams 1 and 2. These beams 1 and 2 have their lightwaves expressed as follows.

$$\text{Beam 1: } S1 = A \times M(t) \exp\{i(2\pi(Fp+Fb)t+\phi)\} \quad (3)$$

$$\text{Beam 2: } S2 = B \times M(t) \exp\{i(2\pi(Fp+Fb)t+\phi)\} \quad (4)$$

where A and B are constants representing the lightwave amplitudes, with A of the beam 1 used for excitation being set greater than B, $\phi$ is a value which is variable depending on the structure of optical system and the variation of intensity, and M(t) is a factor representing the degree of intensity modulation. Since in this embodiment the original laser beam is intensity-modulated in a sinusoidal waveform at frequency F, the term M(t) is expressed as follows.

$$M(t) = 1 + m \cdot \cos(2\pi F t + q) \quad (5)$$

where m is the modulation factor (0<m<1), and q is a constant.

The beam 1 is illuminated on to a sample 34, and the reflected light, which includes a phase variation component P attributable to the photothermal displacement caused by the intensity variation of the excitating beam 1, has its lightwave Sr expressed as follows.

$$Sr = R \cdot M(t) \exp\{i(2\pi(Fp+Fb)t+\phi+\phi r+P)\} \quad (6)$$

where R is the reflection factor of the sample 34 dependent on the transmittance of the optical system, and $\phi r$ is the phase variation relative to the light path length.

A beam sampler 35 located at the output of the laser source 31 samples the original laser beam (beam 3), and it is split by a beam splitter 36 into beams 3' and 3". The beam 3 has its lightwave amplitude expressed as follows.

$$T = C \cdot \exp\{i(2\pi Fpt+\phi c)\} \quad (7)$$

where C and $\phi c$ are constants.

The beam 3' and the reflected light from the sample 34 are merged by a beam splitter 37 so as to interfere with each other, and the interference light is received by an opto-electric transducer 38. The transducer 38 has its output P1 expressed as follows.

$$P1 = D|Sr+T|^2 = D\{|Sr|^2+|C|^2+2R \cdot M(t)C \cdot \cos(2\pi Fbt+\phi+\phi 1+P)\} \quad (8)$$

where D is a constant, and $\phi 1$ is the phase variation relative to the light path length.

Similarly, the beam 2 and beam 3" are merged through the beam splitter 33 so as to interfere with each other, and the interference light is received by an opto-electric transducer 39. The transducer 39 has its output P2 expressed as follows.

$$P2 = E|S2+T|^2 = E\{|S2|^2+|C|^2+2R \cdot M(t)C \cdot \cos(2\pi Fbt+\phi+\phi 2)\} \quad (9)$$

where E is a constant, and $\phi 2$ is the phase variation relative to the light path length.

A specific method of detecting the phase difference of the two signals will be explained. A beat frequency component is extracted from the output P1 by a filter 40, and it becomes a signal V1 after being shaped to have a constant amplitude by a limitter amplifier 41. The signal V1 is expressed as follows.

$$V1 = F1 \cdot \cos(2\pi Fbt+\phi+\phi 1+\phi 1e+P)\} \quad (10)$$

where F1 is a constant, and $\phi 1e$ is a value dependent on the phase variation created in the electrical circuit.

Similarly, a beat frequency component is extracted from the output P2 by a filter 42, and it becomes a signal V2 after being shaped to have a constant amplitude by a limitter amplifier 43. The signal V2 is expressed as follows.

$$V2 = F2 \cdot \cos(2\pi Fbt+\phi+\phi 2+\phi 2e+q)\} \quad (11)$$

where F2 is a constant, $\phi 2e$ is a value dependent on the phase variation created in the electrical circuit, and q is the phase variation produced by a phase shifter 44.

The filters and amplifiers of the same characteristics are used for the processing of the outputs P1 and P2, which accordingly have an equal phase variation ($\phi 1e = \phi 2e$) in the process.

Subsequently, the signals V1 and V2 are mixed by a multiplier 45. The mixed output V3 has a low frequency component VL (residual component after the frequency band of 2Fb has been cue off by a low-pass filter 46) expressed as follows.

$$VL = G \cdot \cos(P+\phi 1-\phi 2-q) \quad (12)$$

where G is a constant. The phase variations $\phi 1$ and $\phi 2$ are detected as d.c. levels of VL by a low-pass filter 47. The phase q is controlled by the phase shifter 44 so that the d.c. level is zero ($\phi 1-\phi 2-q=\pi/2+2n\pi$ (n=1,2, ... )).

The signal VL is express as follows.

$$VL = G \cdot \sin(P) - GP \quad (13)$$

From the signal VL, the phase variation P caused by the photothermal displacement is detected. The photothermal displacement is expressed in terms of the phase variation P as follows.

$$L = P\lambda/4\pi \quad (14)$$

where $\lambda$ is the laser wavelength.

Based on the photothermal displacement L, the characteristics (thermal elastic characteristic, light absorbing characteristic, etc.) of the sample 34 are evaluated. The detection of the phase variation P, calculation of the photothermal displacement L and valuation of the sample 34 are implemented by means of a data processor 48 including a lock-in amplifier, computer, etc. equipped in the final stage of the apparatus A4.

Although in this embodiment the laser beams are propagated in the space, they may be conducted through optical fibers and merged for interference by use of fiber couplers, as in the preceding third embodiment.

Since in this embodiment the photothermal displacement is measured based on the phase of the reflected light of exciting laser beam from the sample, it is not necessary to have another laser beam illuminated to the measuring position of photothermal displacement. Accordingly, this embodiment is free from the problem of misalignment of the exciting beam and measuring beam encountered in the prior art apparatus A01.

The beams 1 and 2 have the same phase variation due to the intensity modulation, and accordingly by measuring the phase of the reflected light of beam 1 from the sample relative to the beam 2, their phase variation cancels out, enabling the detection of only the phase difference caused by the photothermal displacement in the reflected light of beam 1 from the sample. Accordingly, this embodiment is free from the noise problem encountered in the prior art apparatus A02 and A03.

In the phase measurement, the reflected light from the sample and the beam 2 have their light frequency undergoing the beat-down (reduction) based on the scheme of light interference, and the phase is measured after being converted into a.c. signals. This method is practical for attaining a high measuring accuracy as compared with the case of measurement in a high frequency region. In consequence, it is possible to measure the photothermal displacement accurately and stably without implementing intricate signal processings.

We claim:

1. A sample evaluation method based on the measurement of a photothermal displacement on a sample caused by the illumination of an excitation light beam, said method comprising the steps of:

generating two exciting beams and two measuring beams;

implementing intensity modulation for the two exciting beams in different phase relationship and illuminating the modulated light beams to different positions of a sample;

providing different oscillation frequencies for the two measuring beams;

illuminating the two measuring beams to the irradiation positions of the exciting beams correspondingly; and merging reflected lights of the measuring beams from the sample so as to interfere with each other and evaluating the sample based on the phase of the interference light.

2. A sample valuation method according to claim 1, wherein said two exciting beams are rendered intensity modulation in opposite phase relationship.

3. A sample evaluation method according to claim 1 or 2, wherein the exciting beams are provided with an oscillation frequency that is different from oscillation frequencies of the measuring beams.

4. A sample evaluation method according to claim 1, wherein said two exciting beams are rendered intensity modulation by means of an acoustic-optic modulator, and a resulting diffracted and non-diffracted light beams are illuminated on to the sample.

5. A sample evaluation method according to claim 1, wherein the photothermal displacement is measured based on a phase variation of a beat signal included in the opto-electric conversion output of the interference light and having a component of oscillation frequency difference of the two measuring beams.

6. A sample evaluation method according to claim 1, wherein the exciting beams are generated by means of a variable-wavelength light source.

7. A sample evaluation method based on the measurement of a photothermal displacement on a sample caused by the illumination of an excitation light beam, said method comprising the steps of:

intensity-modulating a light beam then splitting the intensity-modulated light beam into first and second beams, and illuminating the first split beam on to a sample;

sampling the light beam and splitting the sampled light beam into third and fourth beams;

measuring a first phase of the reflected light of the first split beam from the sample relative to the phase of the third split beam;

measuring a second phase of the second split beam relative to the phase of the fourth split beam; and measuring the photothermal displacement based on the measured first and second phases.

8. A sample evaluation method according to claim 7, wherein the first and second light beams have a light frequency that is different from a light frequency of the third and fourth split light beams, the third light beam is merged with the reflected light so as to interfere with each other separately, the fourth light beam is merged with the reflected light so as to interfere with each other separately, and the photothermal displacement is measured based on the first and second phase difference of the interference lights.

9. A sample valuation method according to claim 8, wherein the interference lights are received by separate opto-electric transducers, and the photothermal displacement is measured based on the phase difference of output signals of said transducers.

* * * * *